(12) United States Patent
Hashiba et al.

(10) Patent No.: US 7,626,162 B2
(45) Date of Patent: Dec. 1, 2009

(54) MASS SPECTROMETRY SYSTEM AND MASS SPECTROMETRY METHOD

(75) Inventors: Shuhei Hashiba, Wako (JP); Takeshi Sakamoto, Asaka (JP)

(73) Assignee: Hitachi, Ltd., Tokyo (JP)

( * ) Notice: Subject to any disclaimer, the term of this patent is extended or adjusted under 35 U.S.C. 154(b) by 86 days.

(21) Appl. No.: 12/038,829

(22) Filed: Feb. 28, 2008

(65) Prior Publication Data
US 2008/0283740 A1 Nov. 20, 2008

(30) Foreign Application Priority Data
May 16, 2007 (JP) .............................. 2007-129998

(51) Int. Cl.
*B01D 59/44* (2006.01)
*H01J 49/26* (2006.01)
*H01J 49/42* (2006.01)

(52) U.S. Cl. ...................... 250/288; 250/281; 250/282; 436/56; 436/89; 530/350; 435/6; 702/27

(58) Field of Classification Search ................. 250/281, 250/282, 286–288, 292, 294, 299; 436/56, 436/86, 89, 90, 174; 530/350, 355; 435/4, 435/6; 702/27
See application file for complete search history.

(56) References Cited

U.S. PATENT DOCUMENTS

| | | | |
|---|---|---|---|
| 6,355,416 B1 * | 3/2002 | Abramson | 435/6 |
| 6,894,276 B1 * | 5/2005 | Takada et al. | 250/292 |
| 6,917,037 B2 | 7/2005 | Ootake et al. | |
| 7,180,056 B2 | 2/2007 | Ohtake et al. | |
| 2004/0248317 A1 * | 12/2004 | Swamy et al. | 436/173 |
| 2006/0094121 A1 * | 5/2006 | Reid et al. | 436/86 |
| 2006/0134723 A1 * | 6/2006 | Fischer | 435/23 |
| 2006/0289735 A1 * | 12/2006 | Ohtake et al. | 250/282 |
| 2008/0283740 A1 * | 11/2008 | Hashiba et al. | 250/288 |
| 2009/0053817 A1 * | 2/2009 | Reid et al. | 436/86 |

FOREIGN PATENT DOCUMENTS

| | | |
|---|---|---|
| JP | 2005-345332 | 12/2005 |
| JP | 2006-53004 | 2/2006 |
| JP | 3766391 | 2/2006 |
| JP | 2006-329881 | 12/2006 |
| WO | WO 02/25265 A1 | 3/2002 |

* cited by examiner

*Primary Examiner*—Bernard E Souw
(74) *Attorney, Agent, or Firm*—Antonelli, Terry, Stout & Kraus, LLP.

(57) ABSTRACT

When a liquid mixture of two samples such as biological samples labeled with stable isotopes is subjected to a relative quantitative analysis using a liquid chromatography-tandem mass spectrometry system, various constituents are simultaneously ionized. Accordingly, sufficient time required for second mass spectrometry is not ensured, whereby some ions remain unanalyzed after measurement. To address this problem, after second mass spectrometry, amino acid sequencing is performed using the analysis data of the second mass spectrometry, which enables determination on the presence/absence of a specific amino acid labeled with a stable isotope. When the specific amino acid is present, the m/z value of an isotopically-labeled-paired ion in an MS spectrum is calculated, and non-target information for use in second mass spectrometry is created using the calculated m/z information. This avoids redundant second mass spectrometry on sample components derived from the same peptide while allowing second mass spectrometry to be efficiently performed.

18 Claims, 14 Drawing Sheets

Fig. 5

| MASS-TO-CHARGE RATIO m/z | NON-TARGET INFORMATION FOR USE IN SECOND MASS SPECTROMETRY (TARGET/NON-TARGET) |
|---|---|
| 669.31 | NON-TARGET |
| 664.81 | NON-TARGET |
| . | . |
| . | . |
| . | . |
| . | . |
| . | . |

MASS SPECTROMETRY SYSTEM AND MASS SPECTROMETRY METHOD

CLAIM OF PRIORITY

The present application claims priority from Japanese application JP 2007-129998 filed on May 16, 2007, the content of which is hereby incorporated by reference into this application.

BACKGROUND OF THE INVENTION

1. Field of the Invention

The present invention relates to a mass spectrometry system and mass spectrometry method using a mass spectrometer.

2. Description of the Related Art

In recent years, a general method for identifying a protein with a mass spectrometry method has been carried out by using a tandem mass spectrometer. In this technique, a measuring target sample is separated by a liquid chromatograph, and thereafter ionized. The thus-generated ions are introduced into a mass spectrometer, and separated therein according to mass-to-charge ratios m/z (hereinafter simply described as "m/z"), so that intensities of the ions are detected. Such an analysis method is called as first mass spectrometry. Obtained data is processed by a computer and the processed data is outputted as data such as an MS spectrum. In the tandem mass spectrometer, one of ions having a specific m/z value is selected as a precursor ion. Here, the m/z value is obtained through the first mass spectrometry method. Ions are dissociated from the selected precursor ion with a method termed as collision-induced dissociation (CID) or other methods. In the CID, the precursor ion is firstly made to collide with molecules of an inactive gas, and is activated by partially converting the collision energy into internal energy. Then, consequently, the ions are dissociated from the precursor ion. A method for detecting product ions produced by the dissociation of the precursor ion is called as second mass spectrometry. A protein is identified by comparing an $MS^2$ spectrum obtained through the second mass spectrometry method with a theoretical spectrum obtained from sequence information of known proteins by using a statistical method.

As a protein quantification method using a mass spectrometry, an internal standardization method is often used instead of an absolute quantification method. In the internal standardization method, internal standard substances labeled with stable isotopes in advance are added to a sample. For example, two samples including a specific amino-acid residue (cysteine) are chemically labeled using Cleavable ICAT (registered trademark) Reagents made by Applied Biosystems and a relative quantitative analysis is performed on the two samples. This method makes it possible to minimize variations in a recovery rate during pretreatment and variations in ionization during mass spectrometry and to perform relative quantitative analysis with high accuracy. A relative quantification ratio is calculated by using a peak area in an MS spectrum of labeled peptide ions. In this case, it is not always necessary to identify both ions of an isotopically labeled pair.

Analysis techniques using the aforementioned protein identification method and relative quantification method are often used to comprehensive study, with an approach called proteomics, on proteins present in blood (blood plasma and serum), urine, organ and the like with an approach called proteomics. Under such circumstances, there has been explored a method for performing comprehensive analysis on samples with high-throughput. However, high-throughput proteomic approach has not been fully achieved yet because of various difficulties. One of the reasons for such difficulties is that when mass spectrometric measurement is performed to identify and quantify proteins in a short time, sufficient time required for the second mass spectrometry method is not ensured since too many constituents are ionized simultaneously. Accordingly, some ions remain unanalyzed after the measurement. Moreover, when the relative quantitative analysis is performed on two samples labeled with the aforementioned stable isotope elements, the number of ions produced by the ionization is doubled. This makes it more difficult to ensure time necessary to perform the second mass spectrometry on the ions. For this reason, in the present circumstances, some contrivance such as separation of the sample is made in the stage of sample preparation to reduce the number of ions to be ionized simultaneously. However, this approach has a disadvantage of increasing measurement time.

In addition to the contrivance in sample preparation and the development of device, a control method is being developed in which only an analysis-target precursor ion is efficiently subjected to the second mass spectrometry among multiple ions simultaneously produced by the ionization. Specifically, the development of this control method is attempted by improving the algorithm of control software for selecting the target ion to be subjected to the second mass spectrometry.

Many reports relevant to the aforementioned control software have been published.

According to International Patent Publication WO 2002/025265, a determination is made as to whether or not an ion having a specific m/z value is present in an MS spectrum obtained through first mass spectrometry, and then second mass spectrometry is performed in accordance with the determination result. According to Japanese Patent Application Publication No. 2006-329881, intensity information included in an MS spectrum obtained through first mass spectrometry is effectively used to optimize an analysis flow including selection of a precursor ion to be subjected to the next second mass spectrometry. According to Japanese Patent Application Publication No. 2005-345332, an MS spectrum obtained by performing first mass spectrometry on samples labeled with different stable isotope elements, is analyzed in real time to determine a precursor ion to be subjected to the next second mass spectrometry. According to Japanese Patent No. 3766391, a determination is made as to whether or not to perform a third-order mass spectrometry, which is a third-stage mass spectrometry, on the basis of m/z peak information of an MS spectrum obtained through second mass spectrometry. According to Japanese Patent Application Publication No. 2006-053004, when the same sample is repeatedly measured by using a liquid chromatograph under the same separation condition, precursor ions are selected and measured as follows. At a first round of measurement, a precursor ion is automatically selected by using, as an index, intensity of an ion peak in an MS spectrum obtained through first mass spectrometry. At the same time, mass information on the precursor ions subjected to the second mass spectrometry and retention time before the elusion of the precursor ions from the liquid chromatograph are automatically registered in an internal database. At second and following rounds of measurement, the same precursor ions are not subjected to the second mass spectrometry and an ion having the next highest intensity is measured.

SUMMARY OF THE INVENTION

When various constituents are simultaneously ionized while mass spectrometry is performed, sufficient time required for second mass spectrometry is not ensured. Accordingly, some ions will remain unanalyzed after the second mass spectrometry. The conventional techniques have been improved by carrying out some contrivance such as separation of a sample is made in preparing the sample to reduce the number of ions to be ionized simultaneously, by developing the device for reducing time necessary for the second mass spectrometry, and by improving the algorithm of control software for selecting a target ion to be subjected to the second mass spectrometry. However, in performing the relative quantitative analysis on a liquid mixture of two types of samples respectively labeled with stable isotopes different from each other, it is difficult to satisfactorily solve the problem of unanalyzed ions by using the conventional techniques. This is because an advantage of stable isotope labeling serves as a disadvantage that the number of target ions for the second mass spectrometry is increased. Two types of samples respectively labeled with the stable isotopes different from each other have a similar chemical property, and therefore have an advantage that they are eluted from the liquid chromatograph for sample separation in substantially the same retention time. This advantage minimizes variations of ionization between the two types of samples during mass spectrometry. However, this advantage doubles the number of ions simultaneously ionized. Accordingly, this advantage makes it more complicated and difficult to select one of ions as the precursor ion to be subjected to the second mass spectrometry.

It is an object of the present invention is to provide a mass spectrometry system and a mass spectrometry method to solve the aforementioned problem caused when a sample, such as a biological sample, containing multiple constituents is labeled with stable isotopes to perform a relative quantitative analysis, and to shorten an analysis time by efficiently analyzing a slight amount of a constituent included in plenty constituents.

An amino acid sequencing is performed by using second mass spectrometry data, it is determined whether or not a specific amino acid labeled with a stable isotope is present, the m/z value of an ion forming an isotope labeled pair in an MS spectrum is calculated, and a second mass spectrometry target ion is efficiently selected by using the calculated m/z information.

To satisfy these requirements, there is provided a liquid chromatography—tandem mass spectrometry system including an amino acid sequencing unit and an information processing unit. A liquid mixture of multiple samples respectively containing specific amino acids labeled with multiple stable isotopes having masses different from each other is used in the mass spectrometry system. The amino acid sequencing unit performs sequencing of an amino acid or a labeled specific amino acid. The information processing unit calculates the m/z value of a paired ion as an isotope labeled pair in an MS spectrum by using the analysis result in order to determine whether or not a second mass spectrometry should be performed.

Moreover, the amino acid sequencing unit and the information processing unit can determine whether or not a second mass spectrometry should be performed even for a mixture of multiple samples respectively containing specific amino acids independently labeled with three types of labels made of multiple stable isotopes having masses different from one another, and for samples modified with modulators other than the stable isotope labels.

Using the present apparatus makes it possible to obtain improvement in accuracy both of a ratio of relative quantification and peptide identification, as well as to obtain information utilizable as quality control information of the mass spectrometer for measurement and maintenance.

A mass spectrometry system according to the present invention includes, as an example, a separation unit, an ionization unit, a mass spectrometry unit, an amino acid sequencing unit, an information processing unit and a storage unit. The separation unit separates liquid mixture of multiple samples respectively containing specific amino acids labeled with multiple stable isotopes having masses different from each other. The ionization unit ionizes the samples separated by the separation unit. The mass spectrometry unit performs first mass spectrometry on ions produced by the ionization in the ionization unit and performs second mass spectrometry to dissociate specific ions as precursor ions. The amino acid sequencing unit stores mass information of the amino acids labeled with the multiple stable isotopes, and analyzes an amino acid sequence of the precursor ion dissociated through the second mass spectrometry by using information on secondary fragment ions obtained through the second mass spectrometry. The information processing unit processes a result of an analysis performed by the mass spectrometry unit, and determines whether or not the second fragment ions include a specific fragment ion containing the specific amino acid on the basis of a result of an analysis performed by the amino acid sequencing unit. The storage unit creates and stores non-target ion information for use in second mass spectrometry and stores the information when the information processing unit determines that the specific fragment ion is included. In the mass spectrometry system, when the information processing unit determines that the specific fragment ion is included and if the specific fragment ion contains a specific amino acid labeled with heavier one of the multiple stable isotopes, the storage unit creates and stores the non-target ion information for use in second mass spectrometry for an ion containing a specific amino acid labeled with a lighter stable isotope and having a peak adjacent to a peak of the heavier specific ion. When the information processing unit determines that the specific fragment ion is included and if the specific fragment ion contains a specific amino acid labeled with lighter one of the multiple stable isotopes, the storage unit creates and stores the non-target ion information for use in second mass spectrometry for an ion containing a specific amino acid labeled with a heavier stable isotope and having a peak adjacent to a peak of the lighter specific ion.

The present invention makes it possible to avoid performing redundant second mass spectrometry on sample components derived from the same constituent while performing a relative quantitative analysis on a liquid mixture of multiple samples, such as biological samples, respectively labeled with multiple stable isotopes. Accordingly, second mass spectrometry can be efficiently performed on a slight amount of the constituent in a shorter analysis time.

BRIEF DESCRIPTION OF THE DRAWINGS

FIG. 5 is a diagram of an example of contents of determination information stored in a storage unit according to the first embodiment of the present invention.

DETAILED DESCRIPTION OF THE PREFERRED EMBODIMENTS

Hereinafter, a description will be given of embodiments of the present invention with reference to the drawings.

Figure 1:
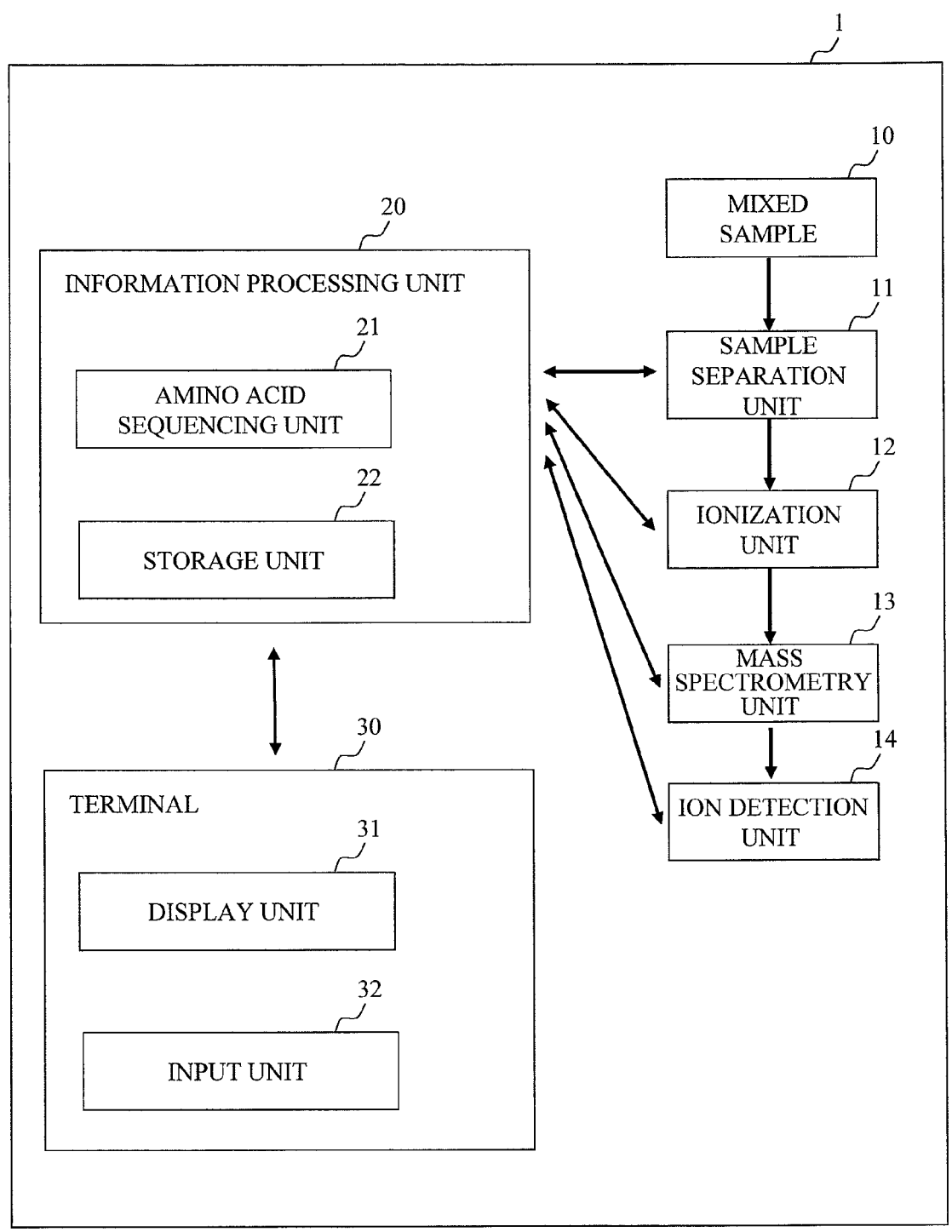
FIG. 1 is a diagram showing a functional block showing an embodiment of a mass spectrometry system according to the present invention.

A first embodiment of the present invention will be explained using FIGS. 1 to 8. FIG. 1 is a functional block diagram showing an embodiment of a mass spectrometry system 1. A mixed sample 10 as an analysis target is a mixture of samples containing a specific amino acid labeled with multiple stable isotopes having masses different from each other. $^3$H (D), $^{13}$C, $^{15}$N, $^{17}$O, $^{18}$O can be used as stable isotopes. To prepare labeled samples, various methods can be employed such as a method of labeling cysteine, lysine or tryptophan, a method of culturing a sample in a labeled amino acid medium, a method of preparing synthetic peptide, and the like. Hereinbelow, a description will be given of an example in which Cleavable ICAT (registered trademark) Reagents made by Applied Biosystems are used in a stable isotope labeling method.

The Cleavable ICAT (registered trademark) Reagents include a heavy labeling reagent ($^{13}$C$_{10}$H$_{17}$N$_3$O$_3$, monoisotopic mass of 236.15) and a light labeling reagent ($^{12}$C$_{10}$H$_{17}$N$_3$O$_3$, monoisotopic mass of 227.15), each of which is used for labeling cysteine contained in proteins. The protein samples respectively labeled with the heavy and light labeling reagents are mixed, and the resultant mixture is cleaved into peptides by digestive enzymes such as trypsin. Next, the peptides containing labeled cysteine are purified. Subsequently, tags used for purification are cut and removed from the peptides so that the mixed sample 10 can be obtained. The mixed sample 10 may further be fractionated and desalted.

The mixed sample 10 is separated and fractionated in a sample separation unit 11 by using liquid chromatography, gas chromatography, capillary electrophoresis or the like. Hereinafter, a description will be given of an example in which the liquid chromatograph is used as a separation system in the sample separation unit 11. In the liquid chromatograph, the sample is once made absorbed on a trap column or separation column. A specific material depending on the composition of a liquid mobile phase introduced into the column is eluted into the liquid mobile phase. Accordingly, by changing the composition of the mobile phase in a stepwise manner, components of the sample absorbed on the column are sequentially eluted in the mobile phase, thereby being separated. Here, the comparison-target peptides are labeled with stable isotopes with masses different from each other, but have the same amino acid sequence. Accordingly, the peptides retain substantially the same chemical property on the column. Thus, the liquid chromatograph allows comparison-target samples to be eluted therefrom as an isotopically labeled pair in substantially the same retention time without separating the samples from each other.

The sample separated in the sample separation unit 11 is introduced into an ionization unit 12, and ionized therein. Thereafter, the ionized sample is introduced into a mass spectrometry unit 13. As an ionization method, an electrospray ionization method, a matrix-assisted laser desorption ionization method, an electron ionization method, a chemical ionization method, a fast atom bombardment method, an atmospheric pressure ionization method or the like may be employed. Hereinbelow, a description will be given of an example in which measurement is performed in a positive ion mode by using an electrospray ionization method as the ionization method in the ionization unit 12.

The ions introduced into the mass spectrometry unit 13 are subjected to mass spectrometry or tandem mass spectrometry to be detected by an ion detection unit 14. Mass spectrometers include a quadrupole mass spectrometer, an ion trap mass spectrometer, a time-of-flight mass spectrometer, a Fourier transform mass spectrometer, and the like, and a tandem mass spectrometer is configured by connecting any of these mass spectrometers. Even a single ion trap mass spectrometer is capable of n-th order mass spectrometry. Hereinbelow, a description will be given of an example in which the mass spectrometer in the mass spectrometry unit 13 is configured of a tandem mass spectrometer composed of an ion trap mass spectrometer and a time-of-flight mass spectrometer. Although the tandem mass spectrometer is employed herein, it is capable of n-th order mass spectrometry since it includes the ion trap mass spectrometer.

In second mass spectrometry, an ion (precursor ion) having a specific m/z is first selected, and thereafter dissociated into fragment ions. The second mass spectrometry is one to be performed on the thus-obtained fragment ions. Furthermore, in third-order mass spectrometry, one of the fragment ions produced in the second mass spectrometry is first selected as a precursor ion, and thereafter dissociated into fragment ions. The third-order mass spectrometry is one to be performed on the thus-obtained fragment ions. As described above, mass spectrometry in which selection and dissociation are performed in different stages is called n-th order mass spectrometry.

As a method for dissociating ions from a precursor ion, there are methods called CID, electron captured dissociation (ECD), electron transfer dissociation (ETD), infrared multiphoton dissociation (IRMPD), in source decay (ISD) and post-source decay (PSD). In the CID method, ions are dissociated by making the precursor ion collide with molecules of an inactive gas such as helium. In the ECD method, an ion is fragmented by being caused to capture an electron. In the ETD method, a sample ion is provided with an electron by use of reaction with another ion and thus is fragmented. In the IRMPD method, an ion is dissociated by being irradiated with strong infrared light. In the ISD method, an ion decays in an ionization chamber concurrently with or immediately after ionization. In the PSD method, an ion spontaneously decays after leaving an acceleration electric field of an ion source. Hereinbelow, a description will be given of an example in which a CID method is used as a method for dissociating a precursor ion in the mass spectrometry unit 13.

An information processing unit 20 controls the sample separation unit 11, the ionization unit 12, the mass spectrometry unit 13 and the ion detection unit 14, as well as performs analysis processing on obtained data. In addition, the information processing unit 20 performs amino acid sequencing in an amino acid sequencing unit 21, stores the analysis result in a storage unit 22, and performs a determination process. Moreover, the information processing unit 20 controls a terminal 30 so that a display unit 31 can display the analysis result, and that an input unit 32 can receive information necessary for amino acid sequencing.

Figure 2:
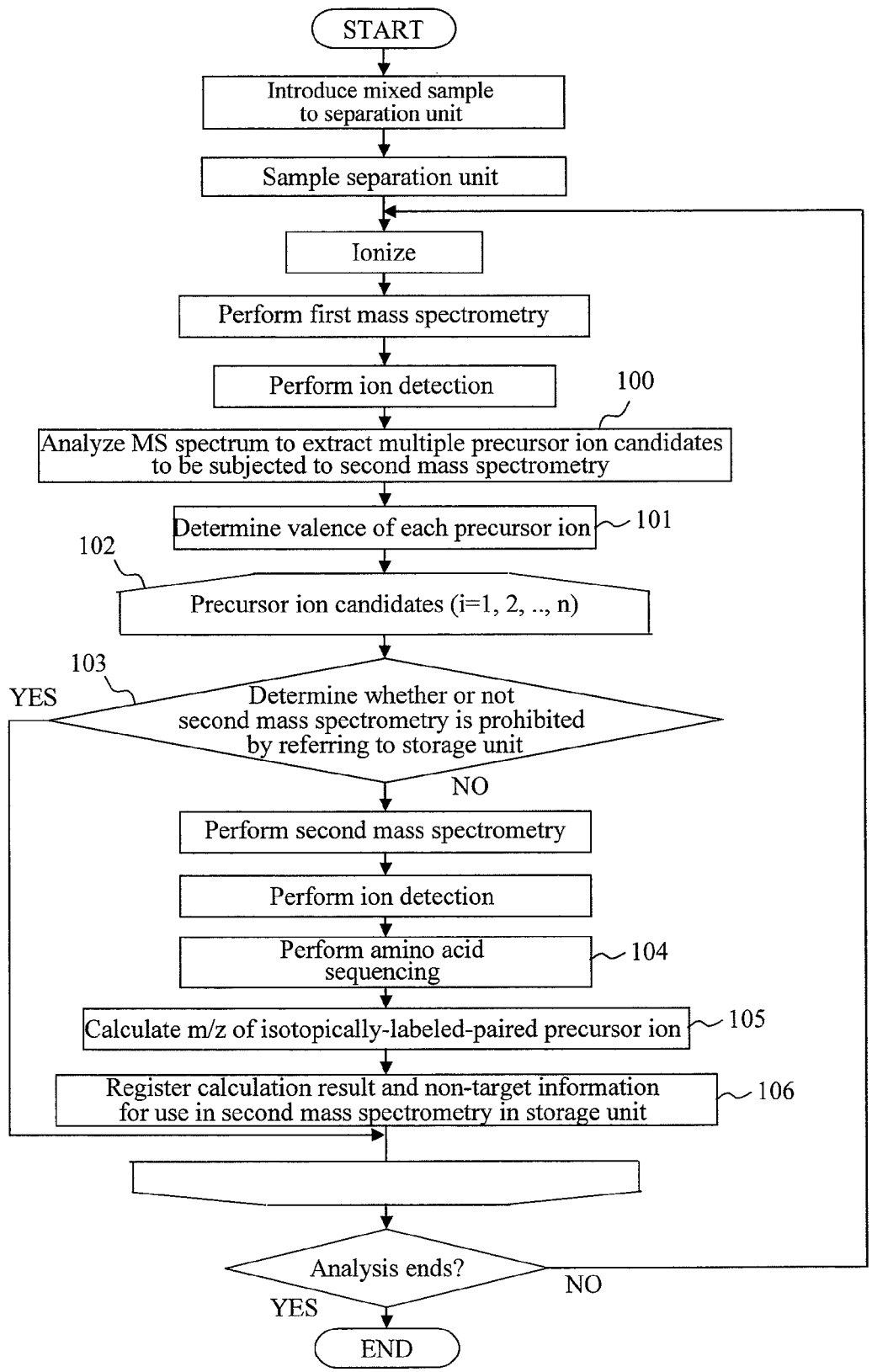
FIG. 2 is a diagram showing a mass spectrometric flow according to a first embodiment of the present invention.

A flowchart of FIG. 2 shows an operation flow of the mass spectrometry system. The mixed sample 10 is introduced into the sample separation unit 11 and separated therein. Thereafter, the separated sample is ionized in the ionization unit 12. The ion is subjected to first mass spectrometry in the mass spectrometry unit 13 and detected by the ion detection unit 14.

The information processing unit 20 analyzes the first mass spectrometry result by using a known method and extracts multiple precursor ion candidates to be subjected to second mass spectrometry (step 100). As a method for extracting the precursor ion candidates, various methods may be employed, such as a method of performing extraction based on the determination whether or not an ion having a specific m/z exists in the MS spectrum, a method of finding and extracting, from the MS spectrum, an isotopically labeled pair that is labeled with stable isotopes, and the like. Hereinbelow, a description will be given of an example in which the MS spectrum is analyzed to extract the precursor ion candidates in descending order of peak intensity as shown in FIG. 3.

Figure 3:
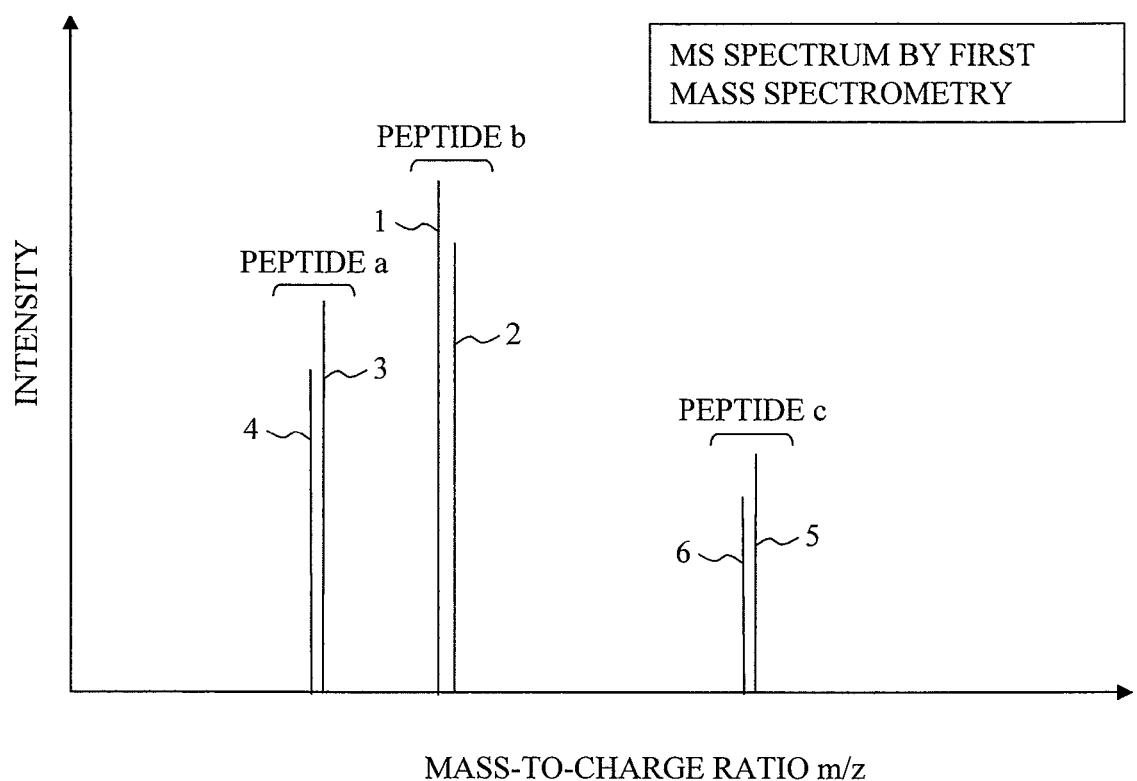
FIG. 3 is a diagram of an example in which an MS spectrum is analyzed to extract precursor ion candidates in descending order of peak intensity according to the first embodiment of the present invention.

FIG. 3 shows an example of the MS spectrum in which peaks derived from three types of peptides (a, b, c) are observed through the first mass spectrometry. Although peaks corresponding to a peptide ion generally include both a monoisotopic peak and isotopic peaks, only the monoisotopic peak is shown here to simplify the drawing. Each type of peptides has peaks of an isotopically labeled pair, that is, a pair of peaks of peptides derived from proteins containing cysteine labeled with heavy and light labeling reagents, respectively. Accordingly, six peaks in total are observed. The peaks are numbered from 1 to 6 in descending order of intensity, and these numbers are used as both peak identification numbers and numbers representing the order of priority as the precursor ion candidates to be subjected to second mass spectrometry.

Figure 4:
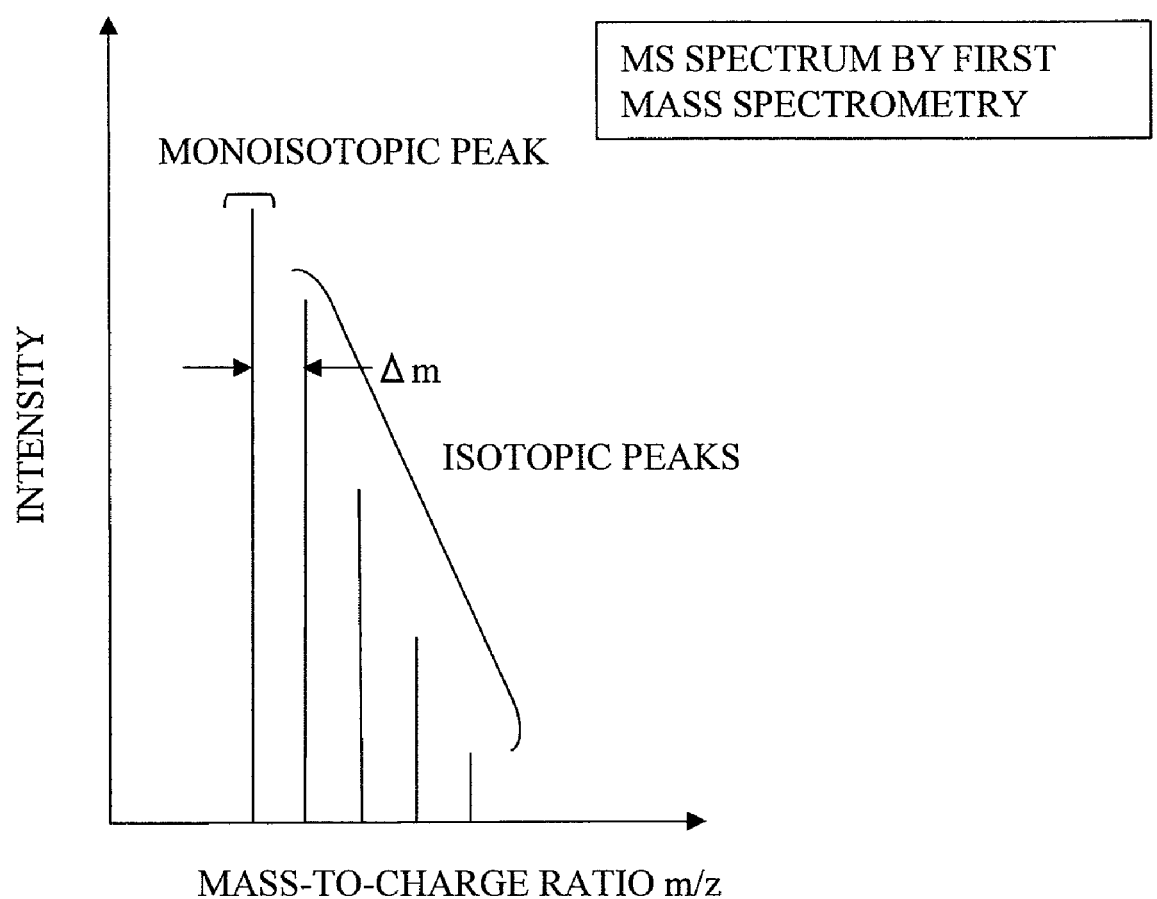
FIG. 4 is a diagram of an example of a method for determining a valence of a precursor ion derived from a peptide according to the first embodiment of the present invention.

Next, the information processing unit 20 determines a valence of each precursor ion by using a known method (step 101). FIG. 4 shows a schematic view of peaks derived from a peptide. The peaks corresponding to a peptide include both a monoisotopic peak and isotopic peaks. Each peak-to-peak interval is $\Delta m$. When a valence is z, a relationship of $\Delta m=1/z$ is established. Accordingly, by calculating $\Delta m$ for each precursor ion, the valence of the precursor ion can be easily determined. Step 101 may be performed before step 100.

Next, the information processing unit 20 performs loop processing the number of times corresponding to the number of precursor ion candidates (step 102).

After that, the information processing unit 20 compares one of the precursor ion candidates with information in the storage unit 22 to determine whether or not second mass spectrometry for the precursor ion candidate is prohibited (step 103). When the second mass spectrometry is not prohibited, the precursor ion candidate proceeds to the next second mass spectrometry. On the other hand, when it is prohibited, the process goes back to step 102 to select another one of the precursor ion candidates and the process goes to step 103. Information necessary for the determination in step 103 is stored in the storage unit 22. FIG. 5 shows an example of contents of such determination information stored in the storage unit 22. The information contains, for each precursor ion, m/z information and attributive information indicating that the precursor ion is excluded from the second mass spectrometry target. As the m/z information of each precursor ion, a monoisotopic mass of the precursor ion is stored. In addition to the above information, the storage unit 22 may store selection criteria such as a valence of a precursor ion, intensity of an MS spectrum, elution time from liquid chromatograph, the number of times of second mass spectrometry, intensity of an $MS^2$ spectrum, effective storage period of information, etc. Moreover, information to be stored in the storage unit 22 may be input from an input unit 32 in advance.

In comparing the m/z value of a precursor ion candidate with an m/z value stored in the storage unit in step 103, the precursor ion candidate is determined as the precursor ion as follows. Assume that $\Delta m/z$ denotes a difference between the m/z value of a precursor ion candidate and an m/z value stored in the storage unit. In this case, if the $\Delta m/z$ is within a range of $\delta$, more specifically, $|\Delta m/z|<\delta$ is true, the precursor ion candidate is regarded to be the same as the precursor ion having the m/z value stored in the storage unit. In this case, $\delta$ may be set to a mass number measurement error of the mass spectrometer.

Next, the precursor ion having proceeded to the second mass spectrometry is subjected to the second mass spectrometry and detected by the ion detection unit. The obtained $MS^2$ spectrum is subjected to amino acid sequencing in the amino acid sequencing unit 21 (step 104). As an amino acid sequencing method, there is used a method of performing de novo sequencing on a partial sequence of each peptide. This is a sequencing method based on determination whether or not any amino acid has a mass corresponding to an interval of fragment ions in the $MS^2$ spectrum. In other words, the method makes it possible to determine a sequence without using database of amino acid sequences for known proteins. Accordingly, the method enables to determine whether or not a specific amino acid labeled with multiple stable isotopes is present even in a peptide having an unknown sequence.

Moreover, the determination whether or not a specific amino acid labeled with multiple stable isotopes is present can be made according to either a monoisotopic mass of the specific amino acid labeled with multiple stable isotopes or a monoisotopic mass of the label, though rarely possible. Here, the former monoisotopic mass is observed in $MS^2$ spectrum. However, this method has a disadvantage of making it impossible to determine whether the found specific amino acid is single or multiple.

Further, the determination whether or not a specific amino acid labeled with multiple stable isotopes is present can be made without using the de novo sequencing. Instead, it is possible by performing sequencing with a focus on whether a mass difference between fragment ions obtained through the de novo sequencing is equal to a monoisotopic mass of the specific amino acid labeled with multiple stable isotopes. However, it is preferable to make a more reliable determination by utilizing, as supplementary information, other information obtained through the de novo sequencing such as information of types of ions (y ion, b ion, etc.), degree of sequence continuity, decoded sequence number, and the like.

Figure 6:
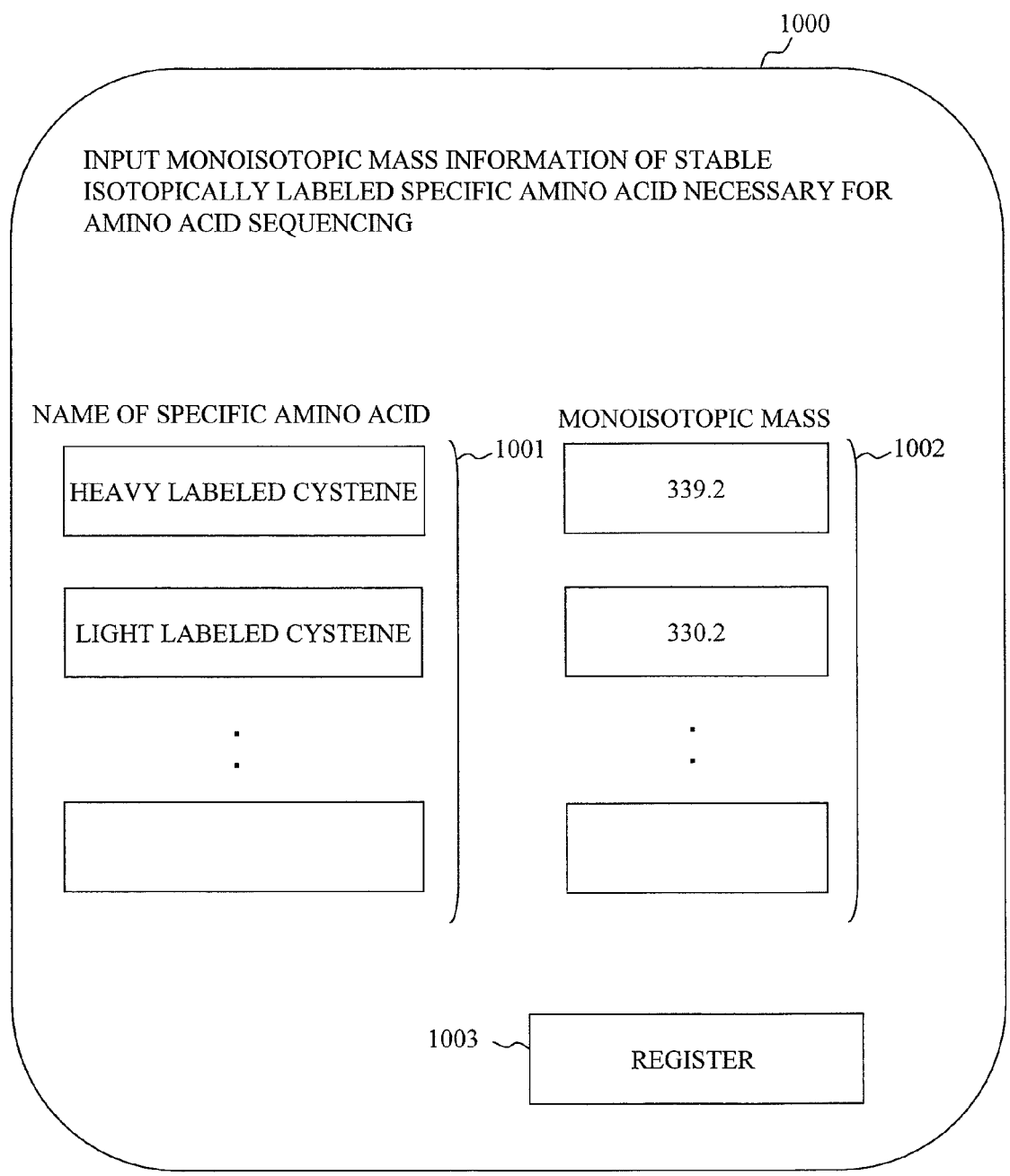
FIG. 6 is a diagram of an example of an input screen for receiving monoisotopic mass information essential for analyzing a specific amino acid sequence according to the first embodiment of the present invention.

FIG. 6 shows an example of an input screen (an input unit displayed on a display unit) for receiving monoisotopic mass information essential for analyzing a specific amino acid sequence labeled with multiple stable isotopes. Information is inputted (selected) through an input screen 1000. The name of a labeled specific amino acid is entered in one of specific amino acid name input fields 1001, and the monoisotopic mass of the labeled specific amino acid is entered in the corresponding one of monoisotopic mass input fields 1002. Thereafter, a registration button 1003 is pressed so that the entered information can be registered. Here, the specific amino acid information may be inputted in advance. The monoisotopic mass information of standard 20 amino acids may also be inputted in advance.

Figure 7:
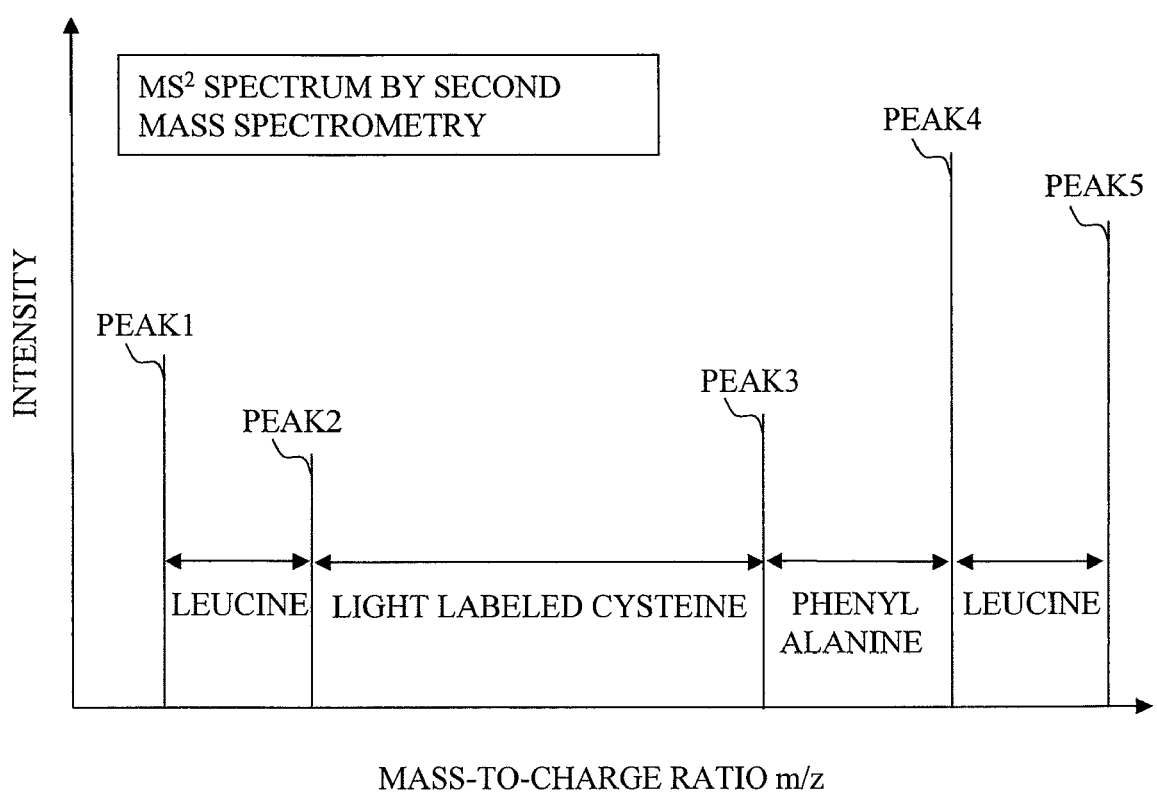
FIG. 7 is a diagram of an example of an analysis of an amino acid sequence containing a specific amino acid according to the first embodiment of the present invention.

FIG. 7 shows an example of an analysis of an amino acid sequence containing a specific amino acid in step 104. It is possible to determine an amino acid corresponding to each peak-to-peak interval on the basis of information on both the peak-to-peak interval of fragment ions in the $MS^2$ spectrum obtained through the second mass spectrometry and the monoisotopic mass inputted through the input unit. FIG. 7 shows that amino acids corresponding to mass differences between peaks 1 and 2, between peaks 2 and 3, between peaks 3 and 4, and between peaks 4 and 5 are leucine, light labeled cysteine, phenylalanine, and leucine, respectively. In this way, a specific amino acid can be found.

Next, when the amino acid sequence analysis unit 21 determines that a specific fragment ion containing a specific amino acid is present (step 105), the information processing unit 20 calculates the m/z value of a precursor ion paired with the precursor ion as an isotopically labeled pair (step 105).

Figure 8:
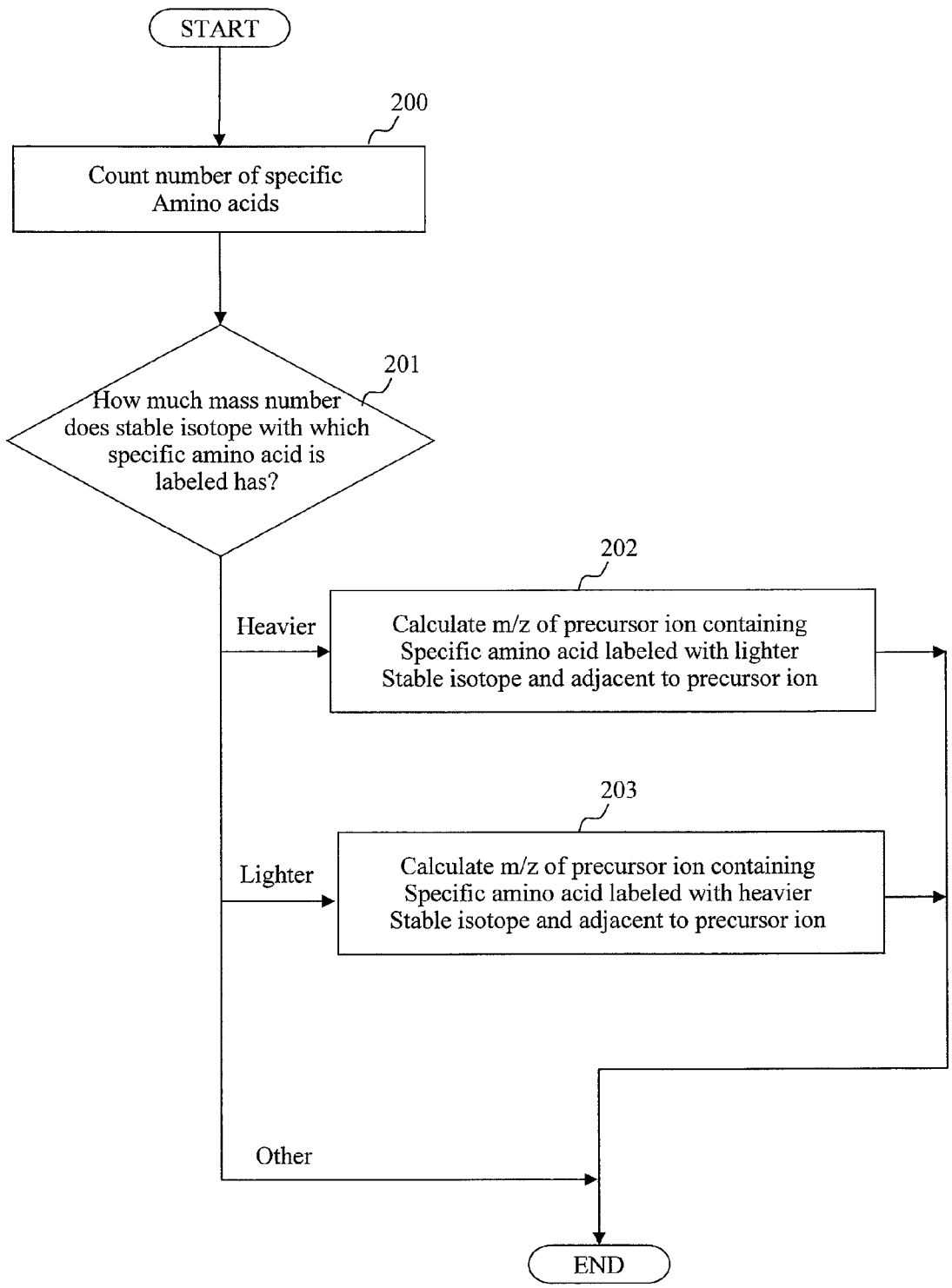
FIG. 8 is a diagram showing a calculation method of the m/z values of paired precursor ions as an isotopically labeled pair according to the first embodiment of the present invention.

FIG. 8 shows a flow of a calculation method of the m/z value of a precursor ion forming an isotopically labeled pair. First, the amino acid sequence analysis unit 21 counts the number of specific amino acids (step 200). Then, which one of steps to follow next is determined on the basis of the masses of the stable isotopes used to label specific amino acids (step 201). When the amino acid sequence analysis unit 21 determines that only heavy labeled cysteine is present, the masses are judged as "heavier" and the process goes to step 202. When the amino acid sequence analysis unit 21 determines that only light labeled cysteine is present, the masses are judged as "lighter" and the process goes to step 203. When the amino acid sequence analysis unit 21 determines that both heavy labeled cysteine and light labeled cysteine are present, the masses are judged as "other" and the process goes to an end step. In step 202, the m/z value of a precursor ion that contains a specific amino acid labeled with a lighter stable isotope and that is adjacent to the heavier precursor ion is calculated (with Equation (1-3) or (1-4)), and thereafter the process ends.

Assume that an m/z value of a precursor ion is $M_O$, that a valence thereof is $z_O$, that a number of specific amino acids is $n_L$, that a monoisotopic mass of the stable isotope label of the precursor ion is $L_O$, that a monoisotopic mass of a hydrogen atom is H and that a monoisotopic mass of a peptide containing an unlabeled specific amino acid is $M_r$. In this case, the m/z value $M_O$ of a precursor ion observed by using an electrospray ionization method in a positive ion mode is given by the following equation $$M_O = \frac{M_r + z_O H + n_L L_O}{z_O}, \quad (1\text{-}1)$$

where $M_r$ is given by the following equation derived from Equation (1-1)

$$M_r = z_O M_O - z_O H - n_L L_O \quad (1\text{-}2).$$

Assume that an m/z value of a precursor ion forming an isotopically labeled pair is $M_P$, that a valence thereof is $z_P$, and that a monoisotopic mass of the stable isotope label thereof is $L_P$. In this case, $M_P$ is given by the following equation $$M_P = \frac{M_r + z_P H + n_L L_P}{z_P}. \quad (1\text{-}3)$$

By substituting Equation (1-2) into Equation (1-3), the following equation is given, $$M_P = \frac{z_O}{z_P} M_O - H\left(\frac{z_O}{z_P} - 1\right) - \frac{n_L}{z_P}(L_O - L_P). \quad (1\text{-}4)$$

$M_P$ can be calculated from either Equation (1-3) or Equation (1-4). In the case where measurement is performed in a negative ion mode, an equation excluding a proton from Equation (1-3) or Equation (1-4) may be used.

Numeral values will be substituted into Equation 1 for describing the calculation method of an m/z value. Assume that the m/z value $M_O$ of the precursor ion is 669.31, that the valence thereof $z_O$ is 2, that the number of specific amino acids $n_L$ is 1, that the monoisotopic mass $L_O$ of the stable isotope label of the precursor ion is 236.15, and that the monoisotopic mass H of the hydrogen atom is 1. In this case, the monoisotopic mass $M_r$ of a peptide containing an unlabeled specific amino acid is 1100.47 from Equation (1-2). Moreover, assume that the valence $z_P$ of a precursor ion adjacent to and paired with the heavier precursor ion as the isotopically labeled pair is equal to $z_O$, and that the monoisotopic mass $L_P$ of the stable isotope label thereof is 227.15. In this case, the m/z value $M_P$ of the paired precursor ion is 664.81 from Equation (1-3).

The aforementioned calculation method of the m/z value of the paired ion as the isotopically labeled pair characteristically makes false-positive less likely to occur because the calculation is performed after direct evidence of the specific amino acid is obtained from the $MS^2$ spectrum.

When the process goes to step 203, the m/z value of a precursor ion that contains a specific amino acid labeled with a heavier stable isotope and that is adjacent to the lighter precursor ion is similarly calculated with the Equation 1, and thereafter the process ends.

Next, the information processing unit 20 registers, in the storage unit 22, the m/z value of the precursor ion calculated in steps 202 or 203 with information indicating the precursor ion is excluded from second mass spectrometry target. The m/z value of the precursor ion may be stored in the storage unit with the non-target ion information for use in second mass spectrometry (step 106).

Thereafter, the process goes back to step 102 and the same process is performed on each precursor ion candidate.

Next, when any sample is left without being eluted from the sample separation unit, the process goes back to the flow for ionizing a sample newly eluted from the sample separation unit. On the other hand, when the separation processing has been performed on all the samples, the analysis ends and thereby second mass spectrometry flow shown in FIG. 2 ends.

According to the aforementioned flow, the second mass spectrometry is performed on the example of the MS spectrum shown in FIG. 3 in order shown as follows. Firstly, peak 1 derived from peptide b is subjected to the second mass spectrometry. On the basis of the analysis result, the m/z value of peak 2 paired with the peak 1 as an isotopically labeled pair is calculated, and peak 2 is excluded from the second mass spectrometry target. Secondly, peak 3 derived from peptide a is subjected to the second mass spectrometry. On the basis of the analysis result, the m/z value of peak 4 paired with the peak 3 as an isotopically labeled pair is calculated, and peak 4 is excluded from the second mass spectrometry target. Then, peak 5 derived from peptide c is subjected to the second mass spectrometry. On the basis of the analysis result, the m/z value of peak 6 paired with the peak 5 as an isotopically labeled pair is calculated, and peak 6 is excluded from the second mass spectrometry target. In the aforementioned flow, second mass spectrometry is performed only a half of the times required in the conventional flow. In the conventional flow, second mass spectrometry should be performed six times.

Figure 9:
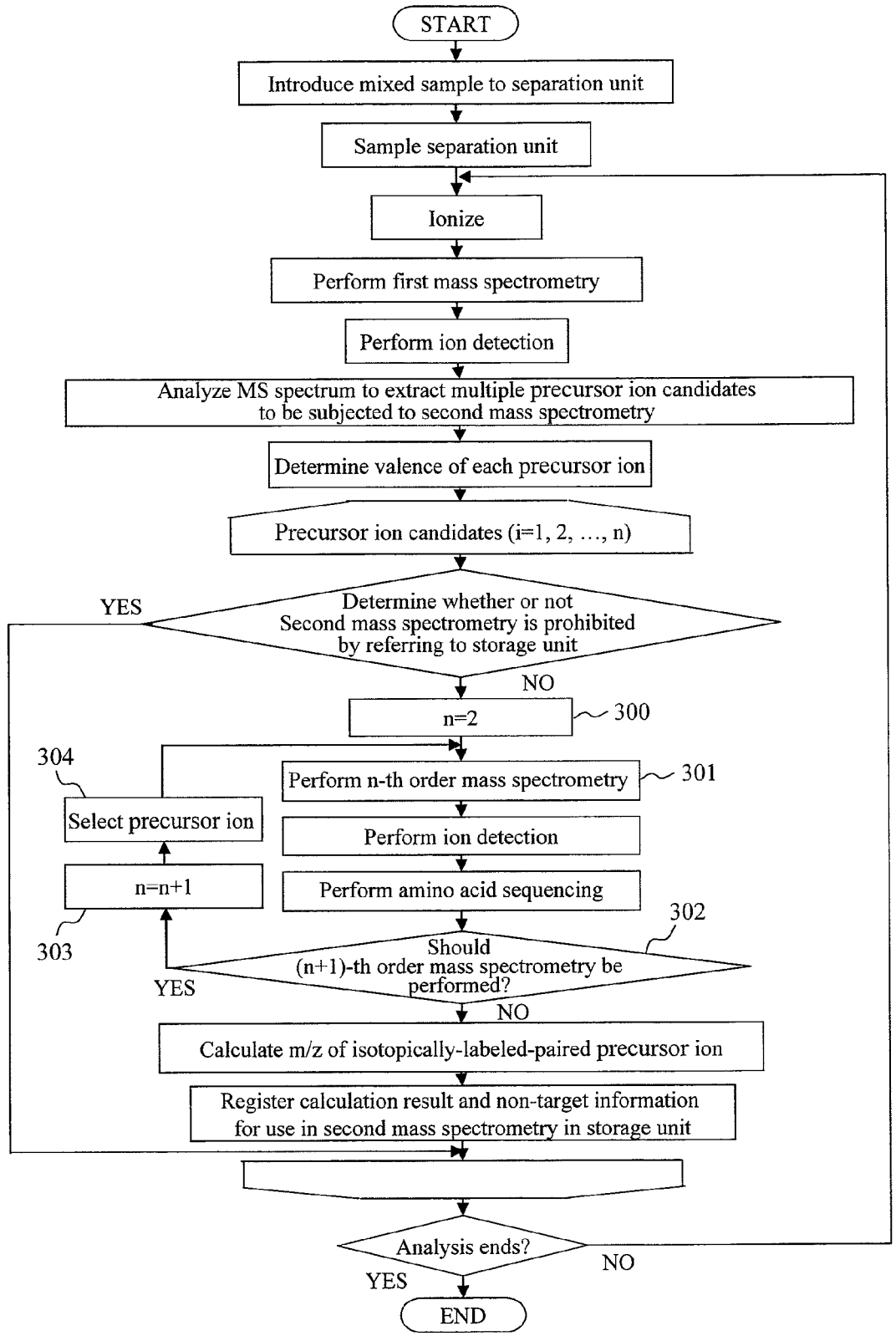
FIG. 9 is a diagram showing a mass spectrometric flow corresponding to n-th order mass spectrometry according to a second embodiment of the present invention.

Next, a second embodiment will be explained using FIG. 9. Here, amino acid sequencing is repeatedly performed on fragment ions having a sufficient intensity by using an ion trap mass spectrometer capable of n-th order mass spectrometry.

Many steps in this embodiment are common to those in the flow according to the first embodiment shown in FIG. 2. Hereinbelow, a description will be given of only steps newly added. First, in step 300, an initial n value 2 for n-th order mass spectrometry is inputted. Next, in step 301, n-th order mass spectrometry is performed. Ion detection and amino acid sequencing in the next steps are performed in the same manner regardless of an n value. In step 302, it is determined whether or not (n+1)-th order mass spectrometry should be performed. For example, (n+1)-th order mass spectrometry may be determined to be performed when maximum intensity among fragment ions is a threshold value or more. When (n+1)-th order mass spectrometry determined to be performed, 1 is added to n in step 303. In step 304, precursor ion to be selected and dissociated is determined. For example, a fragment ion having maximum intensity may be selected as a precursor ion. In this way, amino acid sequencing is repeatedly performed in this embodiment. This makes it possible to obtain more amino acid sequence information than in the first embodiment and to know more accurately whether or not a specific fragment ion containing a specific amino acid is present.

Next, a third embodiment will be explained using FIGS. 10 and 11. Hereinbelow, a description will be given of an example of a stable isotope labeling method using SERVA ICPL (trademark) Triplex-Kit reagents made by SERVA Electrophoresis GmbH to label samples with three types of stable isotope labels of different masses by using three stable isotopes having masses different from one another.

The SERVA ICPL (trademark) Triplex-Kit reagents include a heavy labeling reagent $(1-(^{13}C_6{}^1H_4)$-Nicotinoyloxy-succinimide, monoisotopic mass of 111.0419), a medium-mass labeling reagent $(1-(^{12}C_6{}^1D_4)$-Nicotinoyloxy-succinimide, monoisotopic mass of 109.0715), and a light labeling reagent $(1-(^{12}C_6{}^1H_4)$-Nicotinoyloxy-succinimide, monoisotopic mass of 105.0215), each of which is used for labeling lysine. In this case, monoisotopic masses of three types of a specific amino acid (heavy labeled lysine, medium-mass labeled lysine, light leveled lysine) are inputted and registered through a monoisotopic mass information input screen as shown in FIG. 6. The information may be inputted in advance.

The three types mixed sample is measured by using the method explained in the first and second embodiments. However, a calculation method of the m/z value of a paired precursor ion as an isotope leveled pair in step 105 is different from that of the aforementioned embodiments. Hereinbelow, the calculation method will be described in detail.

Figure 10:
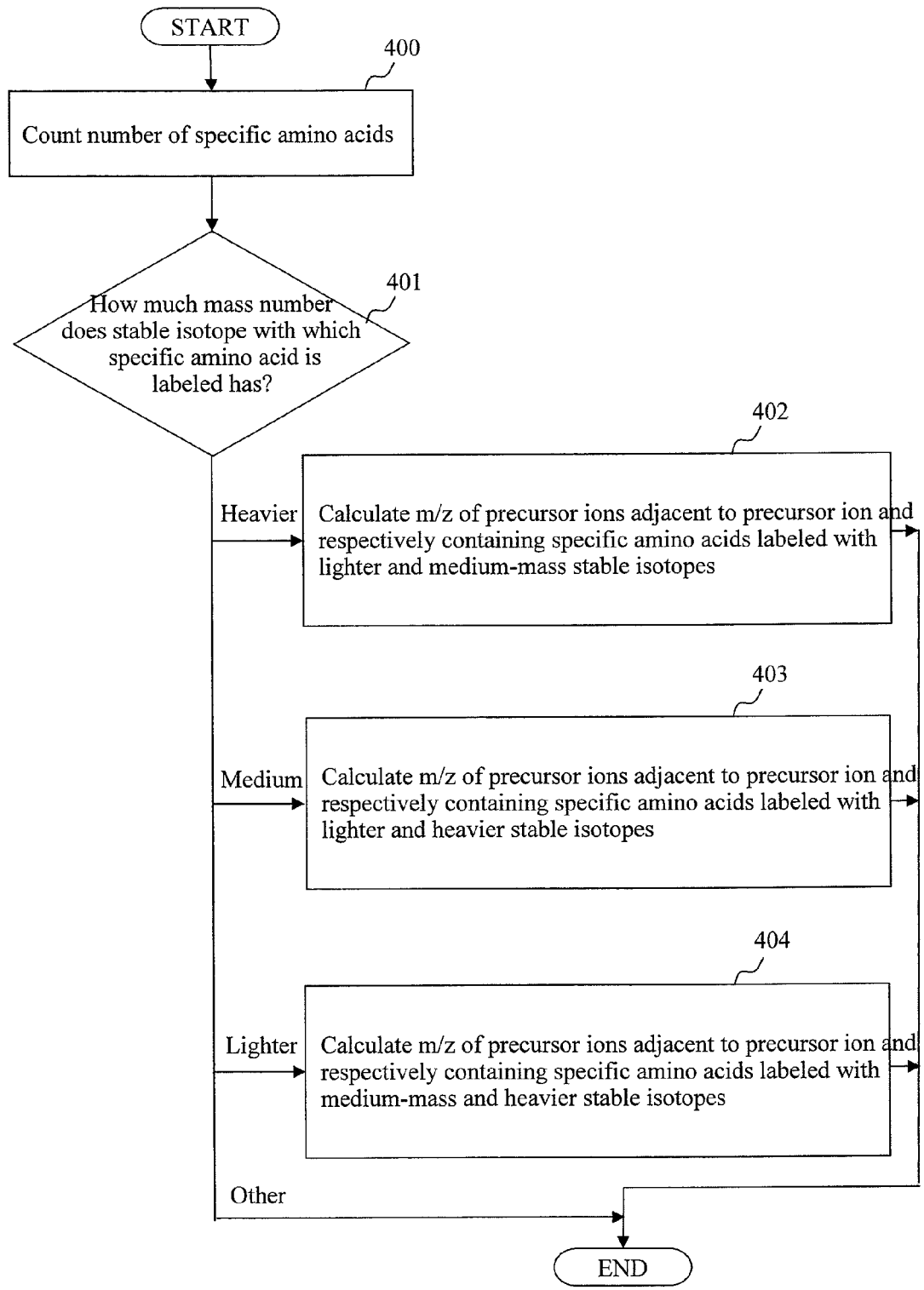
FIG. 10 is a diagram showing a calculation method the m/z values of precursor ions forming an isotope labeled group that is labeled with three types of labels having masses different from one another.
Figure 11:
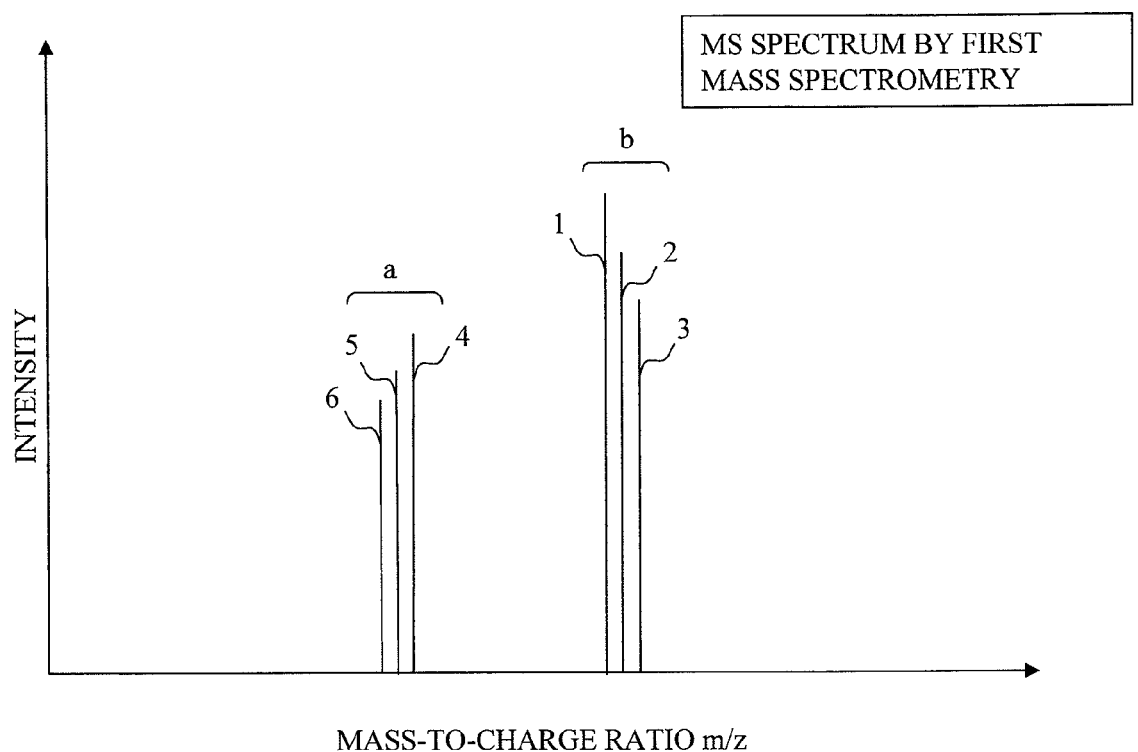
FIG. 11 is a diagram showing an example in which an MS spectrum of samples labeled with three types of labels having masses different from one another is analyzed to extract precursor ion candidates in descending order of peak intensity according to the third embodiment of the present invention.

FIG. 10 shows a flow of a calculation method of the m/z values of precursor ions forming an isotope leveled group that is labeled with three types of labels having masses different from one another. First, the amino acid sequence analysis unit 21 counts the number of specific amino acids (step 400). Then, which one of steps to follow next is determined on the basis of the masses of the stable isotopes used to label specific amino acids (step 401). When the amino acid sequence analysis unit 21 determines that only heavy labeled lysine is present, the masses are judged as "heavier" and the process goes to step 402. When the amino acid sequence analysis unit 21 determines that only medium-mass labeled lysine is present, the masses are judged as "medium" and the process goes to step 403. When the amino acid sequence analysis unit 21 determines that only light labeled lysine is present, the masses are judged as "lighter" and the process goes to step 404. When the amino acid sequence analysis unit 21 determines that two or more types of labeled cysteine are present, the masses are judged as "other" and the process goes to an end step. In step 402, the m/z values of precursor ions that are adjacent to the heavier precursor ion and that contain a specific amino acid labeled with a lighter stable isotope and a medium-mass stable isotope, respectively, is calculated (with Equation 1) and thereafter the process ends.

Numeral values will be substituted into Equation 1 for describing the calculation method of an m/z value. Assume that the m/z value $M_O$ of the precursor ion is 669.31, that the valence thereof $z_O$ is 2, that the number of specific amino acids $n_L$ is 1, that the monoisotopic mass $L_O$ of the stable isotope label of the precursor ion is 111.0419, and that the monoisotopic mass H of the hydrogen atom is 1. In this case, the monoisotopic mass $M_r$ of a peptide containing an unlabeled specific amino acid is 1225.57 from Equation (1-2). Moreover, the m/z value $M_{P_1}$ of a lighter precursor ion adjacent to the heavier precursor ion and forming the isotopically labeled group therewith is 666.29 from Equation (1-3), where $z_p=z_o$, and the monoisotopic mass $L_P$ of the stable isotope label thereof is 105.0215. In addition, the m/z value $M_{P2}$ of a medium-mass precursor ion adjacent to the heavier precursor ion and forming the isotopically labeled group therewith is 668.32 from Equation (1-3), where $z_p z_o$, and the monoisotopic mass $L_P$ of the stable isotope label thereof is 109.0715.

When the process goes to step 403, the m/z values of precursor ions that are adjacent to the medium-mass precursor ion and that contain a specific amino acid labeled with heavier and lighter stable isotopes, respectively, are similarly calculated with the Equation 1, and thereafter the process ends.

When the process goes to step 404, the m/z values of precursor ions that are adjacent to the lighter precursor ion and that contain a specific amino acid labeled with heavier and medium-mass stable isotopes, respectively, are similarly calculated with the Equation 1, and thereafter the process ends.

The analysis order of the second mass spectrometry according to the aforementioned flow will be explained using an example shown in FIG. 11. FIG. 11 shows an example of an MS spectrum in which peaks derived from two types of peptides (a, b) are observed through the first mass spectrometry. Among peaks corresponding to a peptide ion, only the monoisotopic peak is shown to simplify the drawing. Each type of peptides has peaks of an isotopically labeled group so that six peaks in total are observed. The peaks are numbered from 1 to 6 in descending order of intensity, and these numbers are used as both peak identification numbers and numbers representing the order of priority as the precursor ion candidates to be subjected to second mass spectrometry. Firstly, peak 1 derived from peptide b is subjected to the second mass spectrometry. On the basis of the result, the m/z values of peaks 2 and 3 forming the isotopically labeled group with the peak 1 are calculated, and peaks 2 and 3 are excluded from the second mass spectrometry target. Secondly, peak 4 derived from peptide a is subjected to the second mass spectrometry. On the basis of the result, the m/z values of peaks 5 and 6 forming the isotopically labeled group with the peak 4 are calculated, and peaks 5 and 6 are excluded from the second mass spectrometry target. In the aforementioned flow, second mass spectrometry is performed only one-third of the times required in the conventional flow. In the conventional flow, second mass spectrometry should be performed six times.

The third embodiment can be also applied to a mixed sample with n types of stable isotope labels of different masses by using n stable isotopes having masses different from one another. This application example can be implemented in the following procedure. Firstly, monoisotopic masses of n types of a specific amino acid are input and registered through a monoisotopic mass information input screen as shown in FIG. 6. The information may be input in advance. Secondly, the m/z value of each ion forming a stable isotope group is calculated while a monoisotopic mass of the label of the ion is substituted for $L_P$, which denotes the monoisotopic mass of a stable isotope label. Accordingly, the m/z values of all the ions forming a stable isotope group can be calculated from Equation (1-3).

Next, a fourth embodiment will be explained using FIG. 12. Here, the m/z values of isotopically labeled pairs each having a valence different from that of the precursor ion subjected to the second mass spectrometry are also calculated, and those isotopically labeled pairs are excluded from second mass spectrometry target.

Figure 12:
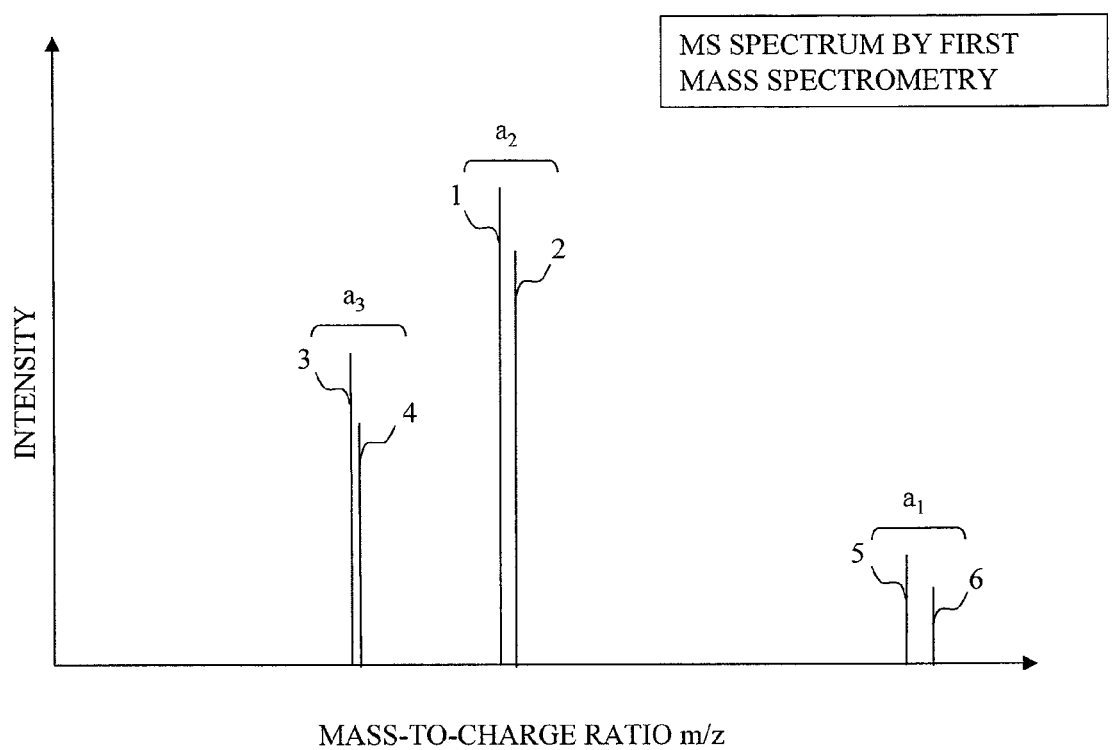
FIG. 12 is a diagram showing an example in which an MS spectrum of isotopically labeled pairs each having a valence different from that of the precursor ion subjected to the second mass spectrometry is analyzed to extract precursor ion candidates in descending order of peak intensity according to a fourth embodiment of the present invention.

FIG. 12 shows an example of an MS spectrum in which peaks derived from one type of peptide a are observed as a result of the first mass spectrometry. Among peaks corresponding to a peptide ion, only the monoisotopic peak is shown to simplify the drawing. $a_1$, $a_2$ and $a_3$ respectively indicate peaks of monovalent, bivalent, and trivalent ions. Each valence-type of peptide ions has peaks of an isotopically labeled pair so that six peaks in total are observed. The peaks are numbered from 1 to 6 in descending order of intensity, and these numbers are used as both peak identification numbers and numbers representing the order of priority as the precursor ion candidates to be subjected to second mass spectrometry. Firstly, peak 1 derived from a bivalent ion is subjected to the second mass spectrometry. On the basis of the result, the m/z value of peak 2 paired with peak 1 as the isotopically labeled pair is calculated by using the method described in the first embodiment, and peak 2 is excluded from the second mass spectrometry target. Moreover, by substituting 3 and 1 for $z_P$, which denotes a valence of an paired ion in Equation (1-3), the m/z values of peaks 4 and 6 are obtained, respectively. Furthermore, by substituting 3 and 1 for $z_P$, which denotes a valence of an paired ion in Equation (1-4) where the monoisotopic masses of stable isotope labels are the same ($L_O = L_P$), the m/z values of peaks 3 and 5 are obtained, respectively. Accordingly, peaks 2 to 6 are excluded from the second mass spectrometry target. In the aforementioned flow, second mass spectrometry is performed only one-sixth of the times required in the conventional flow. In the conventional flow, second mass spectrometry should be performed six times.

Moreover, the fourth embodiment can be carried out by using an ion trap mass spectrometer capable of n-th order mass spectrometry as described in the second embodiment. In addition, the fourth embodiment can be carried out by using a mixed sample labeled with n types of stable isotope labels of different masses by means of n stable isotopes having masses different from one another, as described in the third embodiment.

Next, a fifth embodiment will be explained using FIG. 13. Here, the m/z values of isotopically labeled pairs of modified peptides (Equation (2-4) or (2-5)) are also calculated, and those isotopically labeled pairs are excluded from second mass spectrometry target. As an example of the modification, phosphorylation of threonine is used herein. Monoisotopic mass of phosphorylated threonine is inputted and registered through a monoisotopic mass information input screen as shown in FIG. 6. The information may be inputted in advance.

Assume that a monoisotopic mass of a modulator is M, the sum of monoisotopic masses of k types of modulators is obtained by the following equation, $$\sum_{j=1}^{k} M_j. \tag{2-1}$$

Assume that an m/z value of a precursor ion is $M_O$, that a valence thereof is $z_O$, that a number of specific amino acids is $n_L$, that a monoisotopic mass of the stable isotope label of the precursor ion is $L_O$, that a monoisotopic mass of a hydrogen atom is H and that a monoisotopic mass of a peptide containing an unlabeled specific amino acid is $M_r$. In this case, the m/z value $M_O$, with taking into account peptide modification, of a precursor ion observed by using an electrospray ionization method in a positive ion mode is given by the following equation obtained by adding Equation (2-1) to Equation (1-1)

$$M_O = \frac{M_r + z_O H + n_L L_O + \sum_{j=1}^{k} M_j}{z_O}, \quad (2\text{-}2)$$

where $M_r$ is given by the following equation derived from Equation (2-2)

$$M_r = z_O M_O - z_O H - n_L L_O - \sum_{j=1}^{k} M_j. \quad (2\text{-}3)$$

Assume that an m/z value, out of consideration of peptide modification, of a precursor ion forming an isotopically labeled pair is $M_P$, that a valence thereof is $z_P$, and that a monoisotopic mass of the stable isotope label thereof is $L_P$. In this case, $M_p$ is given by the following equation is given, $$M_P = \frac{M_r + z_P H + n_L L_P}{z_P}. \quad (2\text{-}4)$$

By substituting Equation (2-3) into Equation (2-4), the following equation is given, $$M_P = \frac{z_O}{z_P} M_O - H\left(\frac{z_O}{z_P} - 1\right) - \frac{n_L}{z_P}(L_O - L_P) - \frac{\sum_{j=1}^{k} M_j}{z_P}. \quad (2\text{-}5)$$

$M_P$ can be calculated from either Equation (2-4) or Equation (2-5). In the case where measurement is performed in a negative ion mode, an equation excluding a proton may be used.

Figure 13:
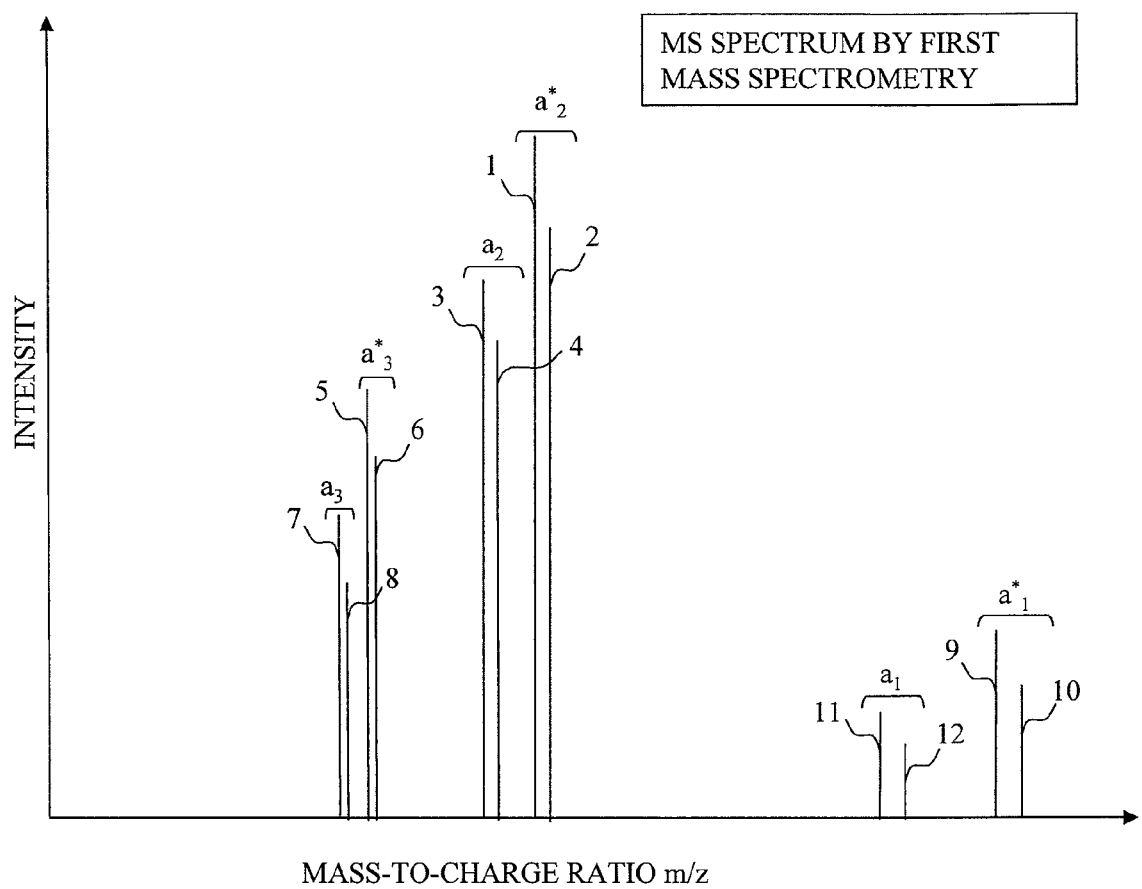
FIG. 13 is a diagram showing an example in which an MS spectrum of isotopically labeled pairs of modified peptides is analyzed to extract precursor ion candidates in descending order of peak intensity according to a fifth embodiment of the present invention.

FIG. 13 shows an example of an MS spectrum in which peaks derived from one type of peptide a and peaks derived from a modified peptide a* are observed as a result of the first mass spectrometry. Among peaks corresponding to a peptide ion, only the monoisotopic peak is shown to simplify the drawing. $a_1$ and $a*_1$ indicate peaks of monovalent ions. $a_2$ and $a*_2$ indicate peaks of bivalent ions. $a_3$ and $a*_3$ indicate peaks of trivalent ions. Each valence-type of peptide ions has peaks of an isotopically labeled pair so that 12 peaks in total are observed. The peaks are numbered from 1 to 6 in descending order of intensity and used as priority, and these numbers are used as a both peak identification numbers and numbers representing the order of priority as the precursor ion candidates to be subjected to second mass spectrometry. Firstly, peak 1 derived from a bivalent ion is subjected to the second mass spectrometry. In this event, it is possible to determine whether or not phosphorylated threonine is present from the amino acid sequence analysis result. When one phosphorylated threonine is determined to be present, a monoisotopic mass of a modulator M in Equation (2-1) is 79.96. Moreover, the number of specific amino acids $n_L$, and the monoisotopic mass of a stable isotope label $L_O$ of the ion are simultaneously obtained from the amino acid sequencing result. By substituting 1 for the monoisotopic mass H of the hydrogen atom, the m/z value of the precursor ion of peak 1 for $M_O$, and the valence thereof for $z_O$ in Equation (2-2) or (2-3), $M_r$ is obtained. The m/z value of peak 4 derived from an ion paired with a bivalent peptide ion containing unphosphorylated threonine can be calculated from Equation (2-4) or (2-5).

Furthermore, the m/z values of peaks 5, 6, 9 and 10 are obtained from that of peak 1. The m/z values of peaks 3, 7, 8, 11 and 12 are obtained from that of the peak 4. Accordingly the peaks are excluded from the second mass spectrometry target. In the aforementioned flow, second mass spectrometry is performed only one-twelfth of the times required in the conventional flow. In the conventional flow, second mass spectrometry should be performed twelve times.

The fifth embodiment can be applied to peptides including multiple modified amino acids by carrying out the following procedure. In this case, monoisotopic masses of multiple modulators are inputted and registered through a monoisotopic mass information input screen as shown in FIG. 6. The information may be inputted in advance.

Incidentally, the modified peptide and unmodified peptide retain, on the column of the liquid chromatograph, chemical properties different from each other. Accordingly, the peptides are sometimes eluted from the liquid chromatograph at slightly different time points. However, the storage unit keeps storing an exclusion list for second mass spectrometry, and the list makes it possible to determine whether or not to exclude ions of peptides from second mass spectrometry target even if the peptides differs in elution time. Moreover, such a difference in elution time empirically obtained may be inputted, as effective storage period of information, into the storage unit 22 through the input unit. This makes it possible to perform second mass spectrometry on a peptide of a different type having the same m/z value measured after the end of the effective period. In addition, if a precursor ion is dissociated by using the CID method in analyzing phosphorylated peptide, a phosphate group thereof is quite likely to be removed. Accordingly, it is desirable to use the ECD or ETD method unlikely to remove the phosphate group.

Moreover, the fifth embodiment can be applied to various post transcriptional modification of proteins such as oxidation, acetylation, ubiquitination, lipidation, glycosylation, lipid peroxidation, glycation, nitrosylation, and the like in addition to phosphorylation. However, it can hardly be applied to some cases. For example, in the case where any of standard 20 amino acids and a modified amino acid has similar masses, it is difficult to distinguish between them. For example, the monoisotopic mass of phenylalanine is 147.06 and that of methionine oxide that is oxidized methionine is 147.03. In such a case, a Fourier transform mass spectrometer having a good mass accuracy is desirably used in a mass analysis unit used for amino acid sequencing.

Moreover, by performing the following procedure, the fifth embodiment can be applied to the case where dehydration (−18 Da) of serine, threonine, a glutamic acid, or an aspartic acid occurs while precursor ions are dissociated, as well as the case where deammoniation (−17 Da) of arginine, lysine, asparagines, or glutamine occurs while precursor ions are dissociated. In this case, monoisotopic masses of dehydrated or deammoniated amino acids are inputted and registered through a monoisotopic mass information input screen as shown in FIG. 6. The information may be inputted in advance. Incidentally, in the fifth embodiment, it is determined whether or not both a specific amino acid and a specific modified amino acid that are labeled with stable isotopes are present. Then, when both are present, exclusion information for second mass spectrometry is created. However, when only the specific modified amino acid is present, exclusion information for second mass spectrometry may be created. Moreover, the fifth embodiment can be carried out by using an ion trap mass spectrometer capable of n-th order mass spectrometry as described in the second embodiment. In addition, the fifth embodiment can be carried out by using a mixed sample labeled with n types of stable isotope labels of different masses by using n stable isotopes having masses different from one another. In the first to fifth embodiments, all of calculated m/z information is regarded as exclusion information for second mass spectrometry. However, the calculated m/z information may be used as second mass spectrometry target information. In this case, the attribute of the m/z information shown in FIG. 5 is set to be second mass spectrometry target. This method may be used in a case where it is desirable that the isotopically labeled pair to be subjected to comparative quantification is preferentially identified.

Next, a sixth embodiment will be explained. Here, first mass spectrometry is performed under conditions where the number of integrations or measurement time is adjusted to cover all of precursor ions and their paired ions as isotopically labeled pairs.

In this embodiment, while the sample is measured by using any of the methods explained in the first to third embodiments, the loop is exited upon calculation of the m/z value of a paired precursor ion as an isotopically labeled pair in step 105. Then, first mass spectrometry is performed under conditions where the number of integrations or measurement time is adjusted. At this time, in order to carry out analysis at high speed, the first mass spectrometry may be performed in an m/z range covering all of precursor ions and their paired ions as isotopically labeled pairs. This improves an S/N ratio of a result of the first mass spectrometry. Accordingly, a relative quantification ratio calculated based on first mass spectrometry data is also improved in accuracy.

Next, a seventh embodiment will be explained. Here, second mass spectrometry is performed under conditions where the number of integrations or measurement time is adjusted to cover all of precursor ions and their paired ions as isotopically labeled pairs. In this embodiment, while the sample is measured by using any of the methods explained in the first to third embodiments, the loop is exited upon calculation of the m/z value of a paired precursor ion as an isotopically labeled pair in step 105. Then, second mass spectrometry is performed under conditions where the number of integrations or measurement time is adjusted so that all of precursor ions and their paired ions as isotopically labeled pairs can be isolated and dissociated. In this embodiment, information of all the precursor ions is utilized. This raises the possibility that a peptide having low ion content can be identified. Such a peptide is difficult to identify individually.

Figure 14:
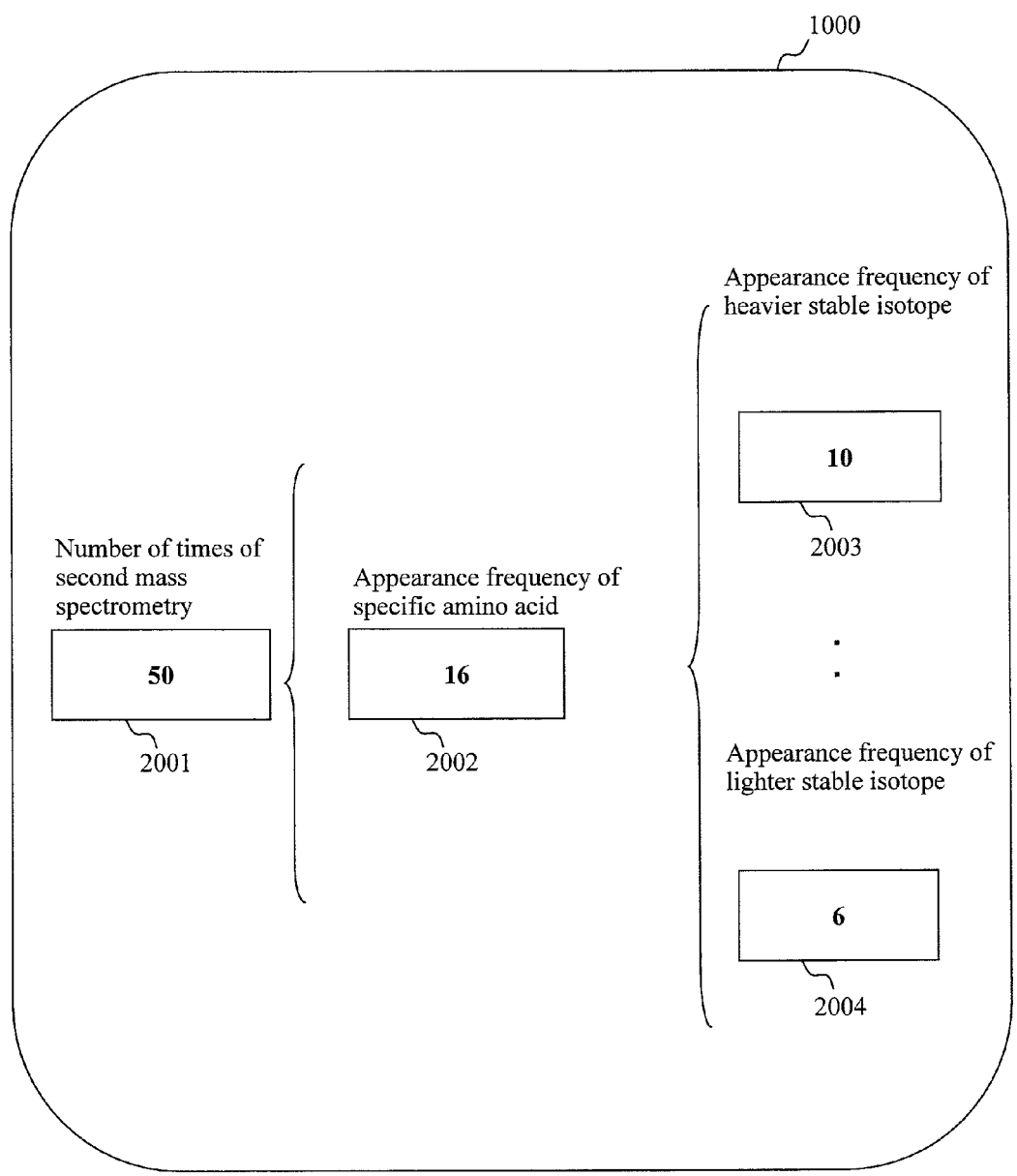
FIG. 14 is a diagram showing a display example of an appearance frequency of a specific amino acid with respect to the number of times of second mass spectrometry according to an eighth embodiment of the present invention.

Next, an eighth embodiment will be explained using FIG. 14. Here, an appearance frequency of a specific amino acid with respect to the number of times of second mass spectrometry is displayed. In the embodiment, while the samples is measured by using any of the methods explained in the first and second embodiments, specific amino acid appearance frequency information is created in step 200 simultaneously with calculation of the m/z value of a paired precursor ion as an isotopically labeled pair in step 105. Moreover, in a second mass spectrometry step, information on the number of times of second mass spectrometry is created. On a monitor screen 1000, the number of times of second mass spectrometry is displayed in a field 2001, the appearance frequency of a specific amino acid is displayed in a field 2002, the appearance frequency of a heavier stable isotope is displayed in a field 2003, and the appearance frequency of a lighter stable isotope is displayed in a field 2004. Even if the number of types of a specific amino acid is increased as shown in the third and fifth embodiments, the appearance frequencies of the increased specific amino acids can be displayed by increasing the number of appearance frequency display fields.

The aforementioned display makes it possible to know, in the course of measurement, the approximate number and percentage of sample components containing a labeled specific amino acid, in a sample. This allows the samples to be reviewed during measurement. This display information can be also utilized as quality control information of the mass spectrometer for measurement and maintenance.

What is claimed is:

1. A mass spectrometry system, comprising:
a separation unit for separating a liquid mixture of multiple samples containing specific amino acids labeled with multiple stable isotopes having masses different from each other;
an ionization unit for ionizing the samples separated by the separation unit;
a mass spectrometry unit for performing first mass spectrometry on ions produced by the ionization in the ionization unit, and for performing second mass spectrometry to dissociate specific ions as precursor ions;
an amino acid sequencing unit for storing mass information of the amino acid labeled with the multiple stable isotopes, and for analyzing an amino acid sequence of the precursor ion dissociated through the second mass spectrometry by using information on secondary fragment ions obtained through the second mass spectrometry;
an information processing unit for processing a result of an analysis performed by the mass spectrometry unit, and for determining whether or not the second fragment ions include a specific fragment ion containing the specific amino acid on the basis of a result of an analysis performed by the amino acid sequencing unit; and
a storage unit for creating and storing non-target ion information for use in second mass spectrometry when the information processing unit determines that the specific fragment ion is included, wherein
when the information processing unit determines that the specific fragment ion is included and if the specific fragment ion contains a specific amino acid labeled with a heavier one of the multiple stable isotopes, the storage unit creates and stores the second mass spectrometry non-target ion information for an ion containing a specific amino acid labeled with a lighter stable isotope and having a peak adjacent to a peak of the heavier specific ion, and
when the information processing unit determines that the specific fragment ion is included and if the specific fragment ion contains a specific amino acid labeled with a lighter one of the multiple stable isotopes, the storage unit creates and stores the second mass spectrometry non-target ion information for an ion containing a specific amino acid labeled with a heavier stable isotope and having a peak adjacent to a peak of the lighter specific ion.

2. The mass spectrometry system according to claim 1, wherein the precursor ion is an ion having a specific mass-to-charge ratio.

3. The mass spectrometry system according to claim 1, wherein
when the information processing unit determines that the specific fragment ion is included and if the specific fragment ion contains a specific amino acid labeled with a heavier one of the multiple stable isotopes, the storage unit creates and stores mass-to-charge ratio information for an ion containing a specific amino acid labeled with a lighter stable isotope and having a peak adjacent to a peak of the heavier specific ion, and when the information processing unit determines that the specific fragment ion is included and if the specific fragment ion contains a specific amino acid labeled with a lighter one of the multiple stable isotopes, the storage unit creates and stores mass-to-charge ratio information for an ion containing a specific amino acid labeled with a heavier stable isotope and having a peak adjacent to a peak of the lighter specific ion.

4. The mass spectrometry system according to claim 1, wherein the information processing unit further determines whether or not an second mass spectrometry candidate ion corresponds to the second mass spectrometry non-target ion information stored in the storage unit and when the second mass spectrometry candidate ion does not correspond to the second mass spectrometry non-target ion information, the mass spectrometry unit performs second mass spectrometry on the second mass spectrometry candidate ion.

5. The mass spectrometry system according to claim 1, wherein the mass spectrometry unit performs an n-th order mass spectrometry on a specific precursor ion, the amino acid sequencing unit analyzes an amino acid sequence of the precursor ion dissociated through the second mass spectrometry by using information on n-th order fragment ions obtained through the n-th order mass spectrometry, and the information processing unit determines whether or not the n-th order fragment ions include a specific fragment ion containing the specific amino acid on the basis of a result of an analysis performed by the amino acid sequencing unit.

6. The mass spectrometry system according to claim 1, wherein the separation unit separates a liquid mixture of multiple samples containing a specific amino acid labeled with three types of stable isotopes having masses different from one another, when the information processing unit determines that the specific fragment ion is included and if the specific fragment ion contains a specific amino acid labeled with a heavier one of the three types of stable isotopes, the storage unit creates and stores the second mass spectrometry non-target ion information for ions having peaks adjacent to a peak of the heavier specific ion and respectively containing specific amino acids labeled with lighter and medium-mass stable isotopes, when the information processing unit determines that the specific fragment ion is included and if the specific fragment ion contains a specific amino acid labeled with a medium-mass one of the multiple stable isotopes, the storage unit creates and stores the second mass spectrometry non-target ion information for ions having peaks adjacent to a peak of the medium-mass specific ion and respectively containing specific amino acids labeled with lighter and heavier stable isotopes, and when the information processing unit determines that the specific fragment ion is included and if the specific fragment ion contains a specific amino acid labeled with a lighter one of the multiple stable isotopes, the storage unit creates and stores the second mass spectrometry non-target ion information for ions having peaks adjacent to a peak of the lighter specific ion and respectively containing specific amino acids labeled with medium-mass and heavier stable isotopes.

7. The mass spectrometry system according to claim 1, wherein when the information processing unit determines that the specific fragment ion is included and if the specific fragment ion contains a specific amino acid labeled with a heavier one of the multiple stable isotopes, the storage unit creates and stores the second mass spectrometry non-target ion information for an ion containing a specific amino acid labeled with a lighter stable isotope and having a peak adjacent to a peak of a heavier specific ion with a valence different from the heavier specific ion, and when the information processing unit determines that the specific fragment ion is included and if the specific fragment ion contains a specific amino acid labeled with a lighter one of the multiple stable isotopes, the storage unit creates and stores the second mass spectrometry non-target ion information for an ion containing a specific amino acid labeled with a heavier stable isotope and having a peak adjacent to a peak of a lighter specific ion with a valence different from the lighter specific ion.

8. The mass spectrometry system according to claim 1, wherein the amino acid sequencing unit further stores monoisotopic mass information of a modified amino acid, the information processing unit determines whether or not the second fragment ions include both a specific fragment ion containing the specific amino acid and a specific modified fragment ion containing the specific modified amino acid on the basis of a result of an analysis performed by the amino acid sequencing unit, when the information processing unit determines that both the specific fragment ion and the specific modified fragment ion are included, and if the specific fragment ion contains a specific amino acid labeled with a heavier one of the multiple stable isotopes, the storage unit creates and stores the second mass spectrometry non-target ion information for an ion containing a specific amino acid labeled with a lighter stable isotope and having a peak adjacent to a peak of the unmodified heavier specific ion, and when the information processing unit determines that both the specific fragment ion and the specific modified fragment ion are included, and if the specific fragment ion contains a specific amino acid labeled with a lighter one of the multiple stable isotopes, the storage unit creates and stores the second mass spectrometry non-target ion information for an ion containing a specific amino acid labeled with a heavier stable isotope and having a peak adjacent to a peak of the unmodified lighter specific ion.

9. The mass spectrometry system according to claim 8, wherein when the information processing unit determines that both the specific fragment ion and the specific modified fragment ion are included, and if the specific fragment ion contains a specific amino acid labeled with a heavier one of the multiple stable isotopes, the storage unit creates and stores the second mass spectrometry non-target ion information for an ion containing a specific amino acid labeled with a lighter stable isotope and having a peak adjacent to a peak of a heavier specific ion with a valence different from the unmodified heavier specific ion, and when the information processing unit determines that both the specific fragment ion and the specific modified fragment ion are included, and if the specific fragment ion contains a specific amino acid labeled with a lighter one of the multiple stable isotopes, the storage unit creates and stores the second mass spectrometry non-target ion information for an ion containing a specific amino acid labeled with a heavier stable isotope and having a peak adjacent to a peak of a lighter specific ion with a valence different from the unmodified lighter specific ion.

10. The mass spectrometry system according to claim 1, wherein any one of the number of integrations and a measurement time for first mass spectrometry is adjusted, according to the second mass spectrometry non-target ion information, so as to cover all of the precursor ions and ions forming isotopically labeled pairs therewith.

11. The mass spectrometry system according to claim 1, wherein any one of the number of integrations and a measurement time for second mass spectrometry is adjusted according to the second mass spectrometry non-target ion information so as to cover all of the precursor ions and ions forming isotopically labeled pairs therewith.

12. The mass spectrometry system according to claim 1, further comprising a display unit, wherein,
when the information processing unit determines that the specific fragment ion is included, appearance frequency information of a specific amino acid is created based on detection information of a specific fragment ion containing a specific amino acid labeled with any of heavier and lighter ones of the multiple stable isotopes, and then is displayed on the display unit.

13. The mass spectrometry system according to claim 1, wherein the specific amino acid is cysteine.

14. The mass spectrometry system according to claim 1, wherein the specific amino acid is lysine.

15. The mass spectrometry system according to claim 1, wherein the specific amino acid is tryptophan.

16. The mass spectrometry system according to claim 1, wherein the specific amino acid is any one of a phosphorylated amino acid, oxidised amino acid, acetylated amino acid, ubiquitinated amino acid, lipidated amino acid, glycosylated amino acid, lipid peroxidated amino acid, glycated amino acid, and nitrosylated amino acid.

17. The mass spectrometry system according to claim 1, wherein the specific amino acid is one of a dehydrated amino acid and a deammoniated amino acid.

18. The mass spectrometry system according to claim 1, further comprising an input unit for receiving information of the specific amino acid.

* * * * *